United States Patent [19]

Eisenhuth et al.

[11] Patent Number: 5,436,346
[45] Date of Patent: Jul. 25, 1995

[54] PROCESS FOR THE PREPARATION OF BENZOTHIAZOLYL-2-SULPHENAMIDES

[75] Inventors: Ludwig Eisenhuth, Obernburg; Manfred Bergfeld, Erlenbach, both of Germany

[73] Assignee: Akzo Nobel N.V., Arnhem, Netherlands

[21] Appl. No.: 240,780

[22] PCT Filed: Dec. 16, 1992

[86] PCT No.: PCT/EP92/02917

§ 371 Date: Jun. 21, 1994

§ 102(e) Date: Jun. 21, 1994

[87] PCT Pub. No.: WO93/13084

PCT Pub. Date: Jul. 8, 1993

[30] Foreign Application Priority Data

Dec. 21, 1991 [DE] Germany ............... 41 42 693.2

[51] Int. Cl.$^6$ ............... A61K 31/425; C07D 277/72
[52] U.S. Cl. ............... 548/168; 514/367
[58] Field of Search ............... 548/168; 514/367

[56] References Cited

FOREIGN PATENT DOCUMENTS

| | | |
|---|---|---|
| 0180869 | 5/1986 | European Pat. Off. . |
| 2726901 | 1/1979 | Germany . |
| 3021429 | 12/1980 | Germany . |
| 3127193 | 5/1982 | Germany . |
| 3325724 | 1/1985 | Germany . |
| 2053205 | 2/1981 | United Kingdom . |

OTHER PUBLICATIONS

"Cleaning Up Oxidations with $H_2O_2$", given at the "International Symposium ORPEC '91", by K. M. Dear, Apr. 29–30, 1991, pp. 1–3.

*Primary Examiner*—Mary C. Lee
*Assistant Examiner*—Laura R. Cross
*Attorney, Agent, or Firm*—Oliff & Berridge

[57] ABSTRACT

The process for the preparation of benzothiazolyl-2-sulphenamides, by reacting a 2-mercaptobenzothiazole or dibenzothiazolyl 2,2'-disulphide with a primary or secondary aliphatic or cycloaliphatic amine in the presence of hydrogen peroxide as oxidizing agent in an aqueous medium is distinguished in that an aqueous hydrogen peroxide solution is metered at a temperature in the range from 30° to 70° C. into an aqueous suspension of the respective amine and the 2-mercaptobenzothiazole or dibenzothiazolyl 2,2'-disulphide in a ratio in the range between 1.0 and 1.5 mol of amine per mole of 2-mercaptobenzothiazole or per equivalent of dibenzothiazolyl 2,2'-disulphide, preferably in a quantity of below 1.35 mol per mole of 2-mercaptobenzothiazole or per equivalent of dibenzothiazolyl 2,2'-disulphide over a period of at least 60 minutes. The total quantity of water in the reaction mixture should not exceed 1500 g per mole of 2-mercaptobenzothiazole. An environmentally friendly and economic process is provided for the preparation of benzothiazolyl-2-sulphenamides in high yield and with high selectivity.

9 Claims, No Drawings

PROCESS FOR THE PREPARATION OF BENZOTHIAZOLYL-2-SULPHENAMIDES

This application is a 371 of PCT/EP92/02917 filed Dec. 16, 1992.

DESCRIPTION

The present invention relates to a process for the preparation of benzothiazolyl-2-sulphenamides from 2-mercaptobenzothiazoles and primary or secondary amines in the presence of an oxidizing agent.

Sulphenamides are employed in large quantities as vulcanization accelerators.

In industry, the benzothiazolyl-2-sulphenamides are prepared from the sodium salt of 2-mercaptobenzothiazole and the corresponding amine using sodium hypochlorite or chlorine. This reaction takes place in accordance with the following reaction equation (Example: preparation of N-cyclohexylbenzothiazolyl-2-sulphenamide):

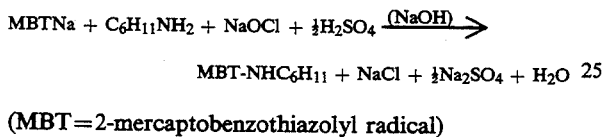

(MBT = 2-mercaptobenzothiazolyl radical)

The principal disadvantage in this reaction is the formation of large quantities of inorganic salts, causing heavy pollution of the effluent and rendering impossible the recycling of the mother liquor and of the wash water. Numerous other processes for the preparation of benzothiazolyl-2-sulphenamides have already been proposed which do not have these disadvantages.

For example, DE-C 33 25 724 describes a process in which, in accordance with the general reaction equation $$MBT + HNRR' + \tfrac{1}{2}O_2 \xrightarrow[(NH_3)]{(Cu\ cat.)} MBT\text{-}NRR' + H_2O,$$

a 2-mercaptobenzothiazole or a dibenzothiazolyl 2,2'-disulphide is reacted with a primary or secondary amine, in the presence of molecular oxygen, a copper catalyst and ammonia, at temperatures of from 0° to 100° C. in excess amine or a mixture thereof with water as reaction medium. Using this process it has been possible to obtain, with high yields and selectivities, a highly pure product in an economic process regime (high space-time yields, recyclability of the mother liquor and continuous procedure). This Patent, to which reference is expressly made hereby, also provides a good overview of the relevant prior art.

In addition, numerous publications describe processes for the preparation of benzothiazolyl-2-sulphenamides from 2-mercaptobenzothiazole and corresponding amines using hydrogen peroxide as oxidizing agent, for example DE-A-31 27 193 which is cited in DE-C 33 25 724, and also EP-A2-0 180 869, DE-A-30 21 429 and DE-A-27 26 901. These processes using hydrogen peroxide are able to form an advantageous alternative to the abovementioned oxygen process to the extent that—unlike DE-C 33 25 724—they operate without additional auxiliaries, such as metal catalyst and ammonia, and at atmospheric pressure. However, these described processes are unsuitable for an industrial application because of the inadequate yields and/or, in some cases, the requirement for very high excesses of amine and hydrogen peroxide. These excesses in turn lead to a reduced selectivity because of secondary reactions, for example to give oxidation products of the amine, sulphites and/or sulphates.

For instance, DE-A-31 27 193 describes a process for the preparation of N-cyclohexylbenzothiazolyl-2-sulphenamide using from 1.5 to 5 mol of cyclohexylamine per mole of 2-mercaptobenzothiazole, where the oxidizing agents mentioned are sodium hypochlorite and hydrogen peroxide (Experimental Examples). In all the Experimental Examples using hydrogen peroxide (Examples 9–11), 2-mercaptobenzothiazole is reacted with three times the stoichiometric quantity of cyclohexylamine and 1.35 times the stoichiometric quantity of hydrogen peroxide; the yields indicated are 87.1%, 87.0% and 84.9%. However, a reworking of Example 9 led to a yield of only 76%.

In EP-A2-0 180 869, a process is described for the preparation of benzothiazolyl-2-sulphenamides from 2-mercaptobenzothiazole or its salts and primary amines up to a degree of conversion which is necessarily only 95%, in which process the preferred oxidizing agents are chlorine bleaching liquor, chlorine and hydrogen peroxide, and in which the only Experimental Example which relates to the use of hydrogen peroxide uses the sodium salt of 2-mercaptobenzothiazole as starting compound, prescribes the addition of sulphuric acid and sodium hydroxide solution and thus also results in the formation of sodium sulphate as by-product. However, the precondition for an economic, environmentally friendly process is—as already mentioned—that such a process should achieve a sufficiently high yield without additional auxiliaries and without by-products which pollute the effluent. Neither in this nor any other respect does EP-A2-0 180 869 provide a concrete indication of this.

The fact that the yield was still inadequate for a problem-free industrial process for the preparation of sulphenamides on the basis of hydrogen peroxide was confirmed only recently in a lecture by Ken M. Dear, "Cleaning Up Oxidations with $H_2O_2$", given at the "International Symposium ORPEC '91", Apr. 29/30 1991, TU Munich, which can be read in the "Symposium Abstracts". In this lecture the maximum achievable yields are given as 77% (as against 95% if chlorine-containing oxidizing agents are used), which is in accordance with the yield of only 76% of N-cyclohexylbenzothiazolyl-2-sulphenamide which was obtained in the abovementioned reworking of Example 9 of DE-A-31 27 193. This lecture at the same time documents the current interest which is evident in a process based on hydrogen peroxide giving improved yields of sulphenamide.

The object of the present invention was thus to provide an environmentally friendly and economic process for the preparation of benzothiazolyl-2-sulphenamides in high yield and with high selectivity, starting from 2-mercaptobenzothiazole or dibenzothiazolyl 2,2'-disulphide, corresponding amines and hydrogen peroxide in accordance with the general reaction equation

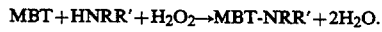

This object is achieved by a process for the preparation of benzothiazolyl-2-sulphenamides, by reacting a 2-mercaptobenzothiazole or dibenzothiazolyl 2,2'-disulphide with a primary or secondary aliphatic or cycloaliphatic amine in the presence of hydrogen peroxide as oxidizing agent in an aqueous medium, characterized in that an aqueous hydrogen peroxide solution is metered at a temperature in the range from 30° to 70° C. into an aqueous suspension of the respective amine and the 2-mercaptobenzothiazole or dibenzothiazolyl 2,2'-disulphide in a ratio in the range between 1.0 and 1.5 mol of amine per mole of 2-mercaptobenzothiazole or per equivalent of dibenzothiazolyl 2,2'-disulphide.

It was very surprising in this context that high yields are obtained even, and indeed precisely, with a sharply reduced excess of the amine starting compound, connected with the additional advantages of a saving on raw material in comparison with the high quantities required according to DE-A-31 27 193, and an increased selectivity.

The 2-mercaptobenzothiazole or dibenzothiazolyl 2,2'-disulphide to be reacted as starting substance according to the invention may, for example, be the compounds mentioned in DE-C-33 25 724 on page 3, lines 34 to 58, or page 3, lines 64 to page 4, line 4 respectively. Preferably however, the unsubstituted 2-mercaptobenzothiazole or dibenzothiazolyl 2,2'-disulphide is employed.

The 2-mercaptobenzothiazole or dibenzothiazolyl 2,2'-disulphide to be reacted as the starting substance in accordance with the invention may, for example, be the following compounds:

2-mercapto-4-methylbenzothiazole
2-mercapto-5-methylbenzothiazole
2-mercapto-6-methylbenzothiazole
2-mercapto-4,5-dimethylbenzothiazole
2-mercapto-4-phenylbenzothiazole
2-mercapto-4-methoxybenzothiazole
2-mercapto-6-methoxybenzothiazole
2-mercapto-5,6-dimethoxybenzothiazole
2-mercapto-6-methoxy-4-nitrobenzothiazole
2-mercapto-6-ethoxybenzothiazole
2-mercapto-4-chlorobenzothiazole
2-mercapto-5-chlorobenzothiazole
2-mercapto-6-chlorobenzothiazole
2-mercapto-7-chlorobenzothiazole
2-mercapto-5-chloro-6-methoxybenzothiazole
2-mercapto- 5-chloro-4-nitrobenzothiazole
2-mercapto- 5-chloro-6-nitrobenzothiazole
2-mercapto- 4,5-dichlorobenzothiazole
2-mercapto- 4,7-dichlorobenzothiazole
2-mercapto- 5-nitrobenzothiazole
2-mercapto- 6-nitrobenzothizole
2-mercapto-4-phenylbenzothizole
2-mercaptonaphthothiazole
2-mercapto-6-hydroxybenzothizole
dibenzothiazolyl 2,2'-disulphide
bis(6-methylbenzothiazolyl) 2,2'-disulphide
bis(4-methylbenzothiazolyl) 2,2'-disulphide
bis(4-methoxybenzothiazolyl) 2,2'-disulphide
bis(6-ethoxybenzothiazolyl) 2,2'-disulphide
bis(5-chlorobenzothiazolyl) 2,2'-disulphide
bis(5-chloro-4-nitrobenzothiazolyl) 2,2'-disulphide
bis(3-chloro-5-nitrobenzothiazolyl) 2,2'-disulphide
bis(6-nitrobenzothiazolyl) 2,2'-disulphide However, it is preferred to employ unsubstituted 2-mercaptobenzothiazole or dibenzothiazolyl 2,2'-disulphide.

Of the amines to be reacted in accordance with the invention, cyclohexylamine is preferably employed.

According to the invention, both the amine and the hydrogen peroxide can be used even in a very slight stoichiometric excess over the quantity of 2-mercaptobenzothiazole or dibenzothiazolyl 2,2'-disulphide employed. A larger excess is possible but, from general economic considerations and also to guarantee the higher selectivities which are sought after, the amine excess should be below 50 mol % and the hydrogen peroxide excess should be preferably below 35 mol % and particularly preferably below 20 mol %, in each case based on the quantity of 2-mercaptobenzothiazole or dibenzothiazolyl 2,2'-disulphide employed.

It was in addition highly surprising that the invention can be successfully achieved using a suspension of the reaction mixture, because all of the prior art cited at the beginning with regard to the preparation of cyclohexylbenzothiazolylsulphenamide refers to the use of the reactants in solution (see e.g. DE-A-31 27 193, Patent claim 1, section (b): "Oxidation of the resulting solution"). Since the production of such solutions is promoted by higher amine excesses, as used for example in DE-A-31 27 193, the low excess of amine according to the invention was thus expected to lead not only to a reduced product yield but also to a reduced solubility of the reactants in water, and also, to this extent, the proportion of amine according to the invention had not been rendered obvious. In fact, with the ratio of amine to 2-mercaptobenzothiazole according to the invention, using quantities of water which are still economically practicable, it is only a suspension and not a solution which is obtained.

In addition to this, it was also surprisingly determined that, in the context of the invention, higher quantities of water actually lead to a drop in the product yield. Therefore a total quantity of water in the reaction mixture of 2000 g per mole of 2-mercaptobenzothiazole should not be exceeded. The process according to the invention is preferably carried out with a total quantity of water of not more than 1500 g and, particularly preferably, not more than 1000 g per mole of 2-mercaptobenzothiazole. Total quantity of water should be understood here as the sum of the water used for the reaction mixture and the water formed chemically by the reaction.

It is of particular advantage, however, that the process according to the invention can be carried out even with surprisingly low quantities of water and thus that high space/time yields can be achieved. With regard to the quantity of water in the lower range, it is apparently only essential for the success of the invention that the solid particles suspended in water form a stirrable suspension.

The concentration of the aqueous hydrogen peroxide solution employed in the process according to the invention can be varied within wide limits. They should not be too low, in order not to lower the yields by relatively high quantities of water. Relatively highly concentrated hydrogen peroxide solutions lead to a drop in the product selectivity and should also be avoided on safety grounds. Concentrations employed with advantage in the process according to the invention are therefore in the range from 5 to 30% by weight of hydrogen peroxide.

The time within which the aqueous hydrogen peroxide solution is metered into the reaction mixture has an effect in the process according to the invention: the longer these chosen metering times, the higher the product yields. Metered addition is preferably carried out within a period of at least 60 minutes and, particularly preferably, of at least 150 minutes. In this manner the yields achieved are essentially greater than 90%, based on 2-mercaptobenzothiazole or dibenzothiazolyl 2,2'-disulphide employed.

As already mentioned, the reaction temperature in the process according to the invention has an effect on the selectivity. It is advantageously in the range from 30° C. to 70° C.; the best results in accordance with the invention are achieved at reaction temperatures in the range from 40° C. to 60° C. The product yields obtained above 70° C. and below 30° C. are poorer; in the latter case this is surprisingly linked with the increase formation of by-products (e.g. sulphite, sulphate and sulphinic and sulphonic acids of 2-mercaptobenzothiazole).

The process according to the invention can be carried out very simply. Auxiliaries such as catalysts or solvents are not required. The addition of water-miscible solvents, such as alcohols, may be advantageous under certain circumstances, for example in order to improve the stirrability of the reaction mixture. However, it is preferred to operate without additional solvents and to choose a quantity of water such that a stirrable mixture of the starting compounds is formed, in the form of a fine, homogeneous suspension; for example 2 parts by weight of water per part by weight of 2-mercaptobenzothiazole/amine mixture.

In general, the 2-mercaptobenzothiazole or dibenzothiazolyl 2,2'-disulphide and the amine are mixed with water in a reaction vessel and heated to reaction temperature, for example 50° C. However, it is likewise also possible initially to introduce the salt formed from 2-mercaptobenzothiazole and the respective amine, especially cyclohexylamine. In this latter case, it is then only necessary to supply the quantity of amine required for the particular stoichiometric excess which is desired. The aqueous hydrogen peroxide solution is then metered at a uniform rate into the stirred mixture, with the content of the reaction vessel continuing to be maintained at reaction temperature. When metered addition is complete there is a relatively short post-reaction phase, for example about 30 minutes, at the same temperature. The reaction mixture is then cooled to room temperature and the solid reaction product is filtered off and washed with water, optionally after preliminary washing with a mixture of the particular amine employed and water. By distillation of the mother liquor, it is possible to recover the amine and also, if desired, unreacted 2-mercaptobenzothiazole or dibenzothiazolyl 2,2'-disulphide.

The purity is determined by titration, HPLC and the melting point.

The product which is obtainable by the process according to the invention without additional purification measures is distinguished by a high purity, with values of more than 98%.

The process according to the invention meets essential criteria for an environmentally friendly and economic process for the preparation of N-cyclohexylbenzothiazolyl-2-sulphenamides: effluent pollution is largely avoided, in particular by the absence of by-products and auxiliaries, such as catalysts and—in general—solvents too; an environmentally acceptable oxidizing agent is employed; the starting compounds are simple chemicals used in a low stoichiometric excess, in a simple reaction carried out at atmospheric pressure to give a pure end product in yields and selectivities which are high and are superior in comparison to the prior art.

The present invention is illustrated in more detail by the Experimental Examples which follow.

EXAMPLE 1

175 g of 95.5% strength 2-mercaptobenzothiazole (1 mol), 500 g of water and 118 g of cyclohexylamine (1.2 mol) were thoroughly mixed in a 1 l reactor with stirrer, reflux condenser and metering device. The resulting fine suspension of the cyclohexylamine salt of 2-mercaptobenzothiazole was brought to 50° C. and reacted, with intensive stirring, with a 12.6% strength aqueous hydrogen peroxide solution (1.1 mol) which was metered in over the course of 5 h. The reaction temperature was maintained at a steady 50° C. during this procedure. Stirring was subsequently continued for a further 30 min at the same temperature. The mixture was cooled to room temperature, and the precipitate was filtered off and washed with a 10% strength aqueous cyclohexylamine solution and then with water and dried.

In this way 250.2 g were obtained of a product which, in its analytical data (elementary analysis, IR, $^1$H NMR) is identical with cyclohexylbenzothiazolylsulphenamide.

The mother liquor also contained 4.3 g of unreacted 2-mercaptobenzothiazole. The degree of conversion of 2-mercaptobenzothiazole was thus 97.4% and the yield of cyclohexylbenzothiazolylsulphenamide was 94.8% of theory.

The purity of the cyclohexylbenzothiazolylsulphenamide product is 99.1% (titration according to Lichty, J. Applied Chem., 2 (1963), 26), the melting point 100°–101° C.

EXAMPLE 2

The procedure of Example 1 is followed, but the hydrogen peroxide solution is metered in over the course of 3.5 h. Cyclohexylbenzothiazolylsulphenamide was obtained in a yield of 92.6% of theory (purity 98.5%).

EXAMPLE 3

The procedure of Example 1 was followed, but the hydrogen peroxide solution was metered in over the course of 1 h. Cyclohexylbenzothiazolylsulphenamide was obtained in a yield of 89.5% of theory.

EXAMPLE 4

The procedure of Example 2 was followed, but the reaction temperature was increased to 60° C. Cyclohexylbenzothiazolylsulphenamide was obtained in a yield of 93.4% of theory (purity 98.2%).

EXAMPLE 5

In this Example, dibenzothiazolyl 2,2'-disulphide is employed instead of 2-mercaptobenzothiazole.

In the reaction apparatus described in Example 1, 166 g of dibenzothiazolyl 2,2'-disulphide (0.5 mol), 1.2 mol of cyclohexylamine and 640 g of water were reacted with intensive stirring and heated to 50° C. At this temperature 140 g of aqueous hydrogen peroxide solution (0.55 mol) were metered in over the course of 3.5 h. The product was separated off as in Example 1 and recovered in a yield of 96.7% of theory (purity 98%).

EXAMPLE 6

The procedure of Example 2 was followed, but the 2-mercaptobenzothiazole and cyclohexylamine were initially introduced in 630 g of water, and the hydrogen peroxide was metered in as a 24.6% strength solution (1.1 mol in 152 g of solution).

Cyclohexylbenzothiazolylsulphenamide was obtained in a yield of 90.4% of theory (m.p. 100°–101° C.).

EXAMPLE 7

The procedure of Example 1 was followed, but only 1.1 mol of cyclohexylamine were employed.

Cyclohexylbenzothiazolylsulphenamide was recovered in a yield of 92.8% (m.p. 100°–101° C.).

EXAMPLE 8

The procedure of Example 1 was followed, but at a reaction temperature of 40° C. Cyclohexylbenzothiazolylsulphenamide was obtained in a yield of 92.1% of theory (m.p. 99°–101° C.).

EXAMPLE 9

The procedure of Example 1 was followed, but at a reaction temperature of 30° C. The yield of cyclohexylbenzothiazolylsulphenamide was 87.1% and the degree of conversion of 2-mercaptobenzothiazole was 93.8% of theory (m.p. 99°–101° C.).

EXAMPLE 10

This Example shows the strong influence of the quantity of water on the yield of product. The procedure of Example 1 was followed, but the quantity of water for preparing the suspension of mercaptobenzothiazole and cyclohexylamine was increased from 500 g to 750 g. The yield of product obtained in this case was only 83% (m.p. 99°–101° C.).

EXAMPLE 11 (Comparative Example)

Example 1 of DE-A-31 27 193 was reworked: in a 250 ml glass reactor, 59.9 g of 50% strength aqueous cyclohexylamine and 0.1 mol of 2-mercaptobenzothiazole were heated to 85° C. with vigorous stirring, with the resulting cyclohexylamine salt of 2-mercaptobenzothiazole going largely into solution. After the mixture had been cooled to 45° C., 92 g of 5% strength hydrogen peroxide (0.135 mol) were metered in over the course of 60 min with vigorous stirring. Stirring was continued for 30 min at the same temperature, and then the reaction mixture was cooled to room temperature, and the precipitate was filtered off, washed with 10% strength cyclohexylamine solution and water, and dried. Cyclohexylbenzothiazolylsulphenamide was obtained in a yield of 75.6% of theory (melting point 99°–100° C.; purity (Lichty titration) 97.6%).

I claim:

1. Process for the preparation of benzothiazolyl-2-sulphenamides, comprising reacting a 2-mercaptobenzothiazole or dibenzothiazolyl 2,2'-disulphide with a primary or secondary aliphatic or cycloaliphatic amine in the presence of hydrogen peroxide as oxidizing agent in an aqueous medium, characterized in that an aqueous hydrogen peroxide solution is metered at a temperature in the range from 30° to 70° C. into an aqueous suspension of the respective amine and the 2-mercaptobenzothiazole or dibenzothiazolyl 2,2'-disulphide in a ratio in the range between 1.0 and 1.5 mol of amine per mole of 2-mercaptobenzothiazole or per equivalent of dibenzothiazolyl 2,2'-disulphide.

2. Process according to claim 1, wherein a total quantity of water in the reaction mixture does not exceed 1500 g per mole of 2-mercaptobenzothiazole or per equivalent of dibenzothiazolyl 2,2'-disulphide.

3. Process according to claim 2, wherein the total quantity of water in the reaction mixture does not exceed 1000 g per mole of 2-mercaptobenzothiazole or per equivalent of dibenzothiazolyl 2,2'-disulphide.

4. Process according to claim 1, wherein the hydrogen peroxide is employed in a quantity of below 1.35 mol per mole of 2-mercaptobenzothiazole or per equivalent of dibenzothiazolyl 2,2'-disulphide.

5. Process according to claim 4, wherein the hydrogen peroxide is employed in a quantity of less than 1.2 mol per mole of 2-mercaptobenzothiazole or per equivalent of dibenzothiazolyl 2,2'-disulphide.

6. Process according to claim 1, wherein the aqueous hydrogen peroxide solution is metered in over a period of at least 60 minutes.

7. Process according to claim 6, wherein the aqueous hydrogen peroxide solution is metered in over a period of at least 150 minutes.

8. Process according to claim 1, wherein the reaction is carried out at a temperature in the range from 40° C. to 60° C.

9. Process according to claim 1, wherein the amine employed is cyclohexylamine.

* * * * *